(12) United States Patent
Armbruster et al.

(10) Patent No.: US 10,613,101 B2
(45) Date of Patent: *Apr. 7, 2020

(54) NON-OXIDIZED, BIOLOGICAL ACTIVE PARATHYROID HORMONE DETERMINES MORTALITY IN HEMODIALYSIS PATIENTS

(71) Applicant: Immundiagnostik AG, Bensheim (DE)

(72) Inventors: Franz Paul Armbruster, Bensheim (DE); Berthold Hocher, Kleinmachnow (DE); Heinz Jürgen Roth, Heidelberg (DE)

(73) Assignee: Immundiagnostik AG, Bensheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/773,619

(22) PCT Filed: Mar. 7, 2014

(86) PCT No.: PCT/EP2014/054508
§ 371 (c)(1),
(2) Date: Sep. 8, 2015

(87) PCT Pub. No.: WO2014/135701
PCT Pub. Date: Sep. 12, 2014

(65) Prior Publication Data
US 2016/0025748 A1 Jan. 28, 2016

(30) Foreign Application Priority Data
Mar. 8, 2013 (EP) ..................... 13158401

(51) Int. Cl.
*G01N 33/53* (2006.01)
*G01N 33/74* (2006.01)

(52) U.S. Cl.
CPC ....... *G01N 33/74* (2013.01); *G01N 2333/635* (2013.01); *G01N 2800/347* (2013.01); *G01N 2800/52* (2013.01)

(58) Field of Classification Search
CPC ............. G01N 33/74; G01N 2800/347; G01N 2333/635; G01N 2800/52; G01N 33/53
See application file for complete search history.

(56) References Cited

U.S. PATENT DOCUMENTS

2006/0211054 A1\* 9/2006 Armbruster ............ G01N 33/74
435/7.5

FOREIGN PATENT DOCUMENTS

WO   WO 02/082092 A2   10/2002

OTHER PUBLICATIONS

Tomasello et al ( Diabetes Spectrum 2008, vol. 21 No. 1 p. 19-25).\*
Floege et al (Nephrol Dial Transplant (2011) 26: 1948-1955).\*
Van Regenmortel, p. 464, abstract in particular; Methods: A Companion to Methods of Enzymology 9:465-472, 1996.\*
E. A. Padlan, Adv Prot Chem 49:57-133; 1996.\*
Corada et al., Blood, 2001; 97:1679-84.\*
Berthold Hocher et al., "Measuring Parathyroid Hormone (PTH) in Patients with Oxidative Stress—Do We Need a Fourth Generation Parathyroid Hormone Assay?", PLOS ONE, Public Library of Science, vol. 7, No. 7, Jul. 6, 2012, pp. 1-10.

\* cited by examiner

*Primary Examiner* — Julie Wu
*Assistant Examiner* — Carmencita M Belei
(74) *Attorney, Agent, or Firm* — Blank Rome LLP

(57) ABSTRACT

A new method of in vitro monitoring and assessing the need of a medication which interferes with the regulation of the parathyroid hormone level in a kidney patient subject to oxidative stress, notably hemodialysis patients. FIG. 1 shows the distribution of n-oxPTH concentrations in 340 hemodialysis patients (224 men and 116 women) with a median age of 66 years (IQR, 56 to 75 years), a median time since initiation of dialysis (dialysis vintage) of 266 days (IQR, 31 to 1209 days), and a median dialysis dose (kt/V) of 1.2 (IQR, 1.1 to 1.3). The cause of chronic kidney disease was nephrosclerosis in 113 cases (33%), diabetic nephropathy in 107 cases (31%), chronic glomerular nephritis in 29 cases (9%), polycystic kidney disease in 9 cases (3%) and other/unknown in 82 cases (24%). The median n-oxPTH concentration was 5.9 ng/L (IQR, 2.4 to 14.0 ng/L). n-oxPTH concentrations were not different in men and women (5.9 ng/L; IQR, 2.4 to 14.2 ng/L; n=224; vs. 5.5 ng/L; IQR, 2.4 to 14.0 ng/L; n=116; p=0.915).

5 Claims, 3 Drawing Sheets

NON-OXIDIZED, BIOLOGICAL ACTIVE PARATHYROID HORMONE DETERMINES MORTALITY IN HEMODIALYSIS PATIENTS

FIELD OF THE INVENTION

The invention relates to means and methods of monitoring parathyroid hormone concentration in plasma samples of patients with chronic kidney disease (CKD).

BACKGROUND OF THE INVENTION

Excess mortality in patients with chronic kidney disease stage 5 is an important unsolved problem. Annual mortality of patients with chronic kidney disease stage 5 is about 10 to 20%. The parathyroid hormone (PTH) seems being a factor responsible for the excess mortality in patients requiring hemodialysis as a recent huge study demonstrated a J-shaped association between PTH and mortality. Consequently, parathyroid hormone (PTH) has been described as a uremic toxin with multiple systemic effects including bone disorders (renal osteodystrophy), myopathy, neurologic abnormalities, anemia, pruritus, and cardiomyopathy. Hyperparathyroidism is common in CKD and results in significant morbidity and mortality if left untreated. Low as well as high PTH levels measured by current PTH assays are associated with a progression of cardiovascular diseases and substantially increased all-cause mortality in patients on hemodialysis (Floege J. et al, *ARO Investigators. Serum iPTH, calcium and phosphate, and the risk of mortality in a European haemodialysis population*. Nephrol Dial Transplant. 2011; 26:1948-1955; Torres P A et al, *Calcium-sensing receptor, calcimimetics, and cardiovascular calcifications in chronic kidney disease*. Kidney Int. 2012; 82:19-25; Souberbielle J C et al. in *Parathyroid hormone measurement in CKD*. Kidney Int. 2010; 77:93-100)

Thus, guidelines have been established aiming to keep PTH in concentrations associated with the lowest morbidity and highest survival. The Kidney Disease Outcomes Quality Initiative (KDOQI) guidelines recommend measuring regularly PTH concentrations of patients with chronic kidney disease (CKD) and adjusting the patients' medication (e.g. vitamin D, phosphate binders, calcimimetics) such that plasma PTH levels are kept within a target range in accordance with the stage of CKD (e.g., 150 to 300 ng/L in patients with CKD stage 5). If pharmacological approaches do not work adequately, parathyreodectomy may be considered.

Secondary hyper-parathyroidism may also occur as an adaptive response to deteriorating renal function when circulating 1,25-dihydroxy vitamin D decreases as early as in stage 2 of CKD and continues to fall as the glomerular filtration rate (GFR) decreases. Chronic kidney disease is associated with a progressive loss of 1α-hydroxylase activity, because of functional reasons such as enzyme inhibition by hyperphosphataemia, hyperuricaemia, metabolic acidosis and sometimes also 25-hydroxyvitamin D deficiency. More important is, however, simply the loss of healthy renal tissue—and hense 1α-hydroxylase—explaining functional reduction of 1α-hydroxylase activity in CKD. As GFR decreases below 60 mL/min/1·73·m$^2$ phosphate is retained which stimulates directly or via the klotho/FGF23 system secretion of PTH. Additionally the 1,25-dihydroxy vitamin D deficiency contributes in this situation to an increased secretion of PTH, since PTH secretion/gene expression in the parathyroid glad is negatively controlled by 1,25-dihydroxy vitamin D.

Hypocalcaemia develops as the GFR decreases below 50 mL/min/1·73·m$^2$, stimulating a secretion of parathyroid hormone (PTH) from cells of the parathyroid gland into the blood circulation. In the intact form human parathyroid hormone (hPTH) consists of a single polypeptide chain having 84 amino acids and a molecular weight of ca. 9500 Dalton (see SWISS-PROT: P01270, PTHY-HUMAN). With disease progression, intact hPTH(aa 1-84) half-life increases and immunoreactive C-terminal fragments of the hormone tend to accumulate in serum. A chronic elevation of parathyroid activity then results in bone loss, fractures, vascular calcification, cardiovascular disease, and hence an increased cardiovascular mortality (cf Fraser W D, *Hyperparathyroidism*. Lancet. 2009; 374:145f).

Part of the problem with the use of PTH measurements has been confusion concerning the interpretation of the assays utilized. The measurement of PTH in blood has evolved since the early 1960s when RIAs were first developed for measurement of PTH (Berson S A et al, Proc Natl Acad Sci USA. 1963; 49:613-617). However, these first-generation assays proved not to be reliable owing to different characteristics of the antisera used and the realization that PTH circulates not only in the form of the intact 84-amino-acid peptide but also as multiple fragments of the hormone, particularly from the mid and carboxy (C)-terminal regions of the PTH molecule. The PTH peptide following secretion is degraded within minutes in the kidney in active and inactive fragments and the respective fragments have further varying half-lifes. A second generation of PTH immunoassays was developed using two antibodies one binding in the aminoterminal portion of the PTH peptide with the biologic activity and the other in its carboxyterminal portion (John M R et al. (1999), J. Clin. Endocrinol. Metab., 84. 4287-4290; Gao P et al. 2000, Poster M455, ASBMR 22nd Annual Meeting; Roth H J et al. (2000), Poster P1288; 11th International Congress of Endocrinology, Sydney). However, there was still a discrepancy between measured immunoreactive PTH concentration in serum and clinical findings (Goltzman D et al, in *Discordant disappearance of bioactive and immunoreactive parathyroid hormone after parathyroidectomy*, J Clin Endocrinol Metab 1984, 58(1):70-75. Thus, a third generation of intact PTH assay has been developed which however fails to improve the diagnosis of bone diseases or other clinical signs of secondary hyperparathyroidism in uraemic patients (Brossard J H et al., *Influence of glomerular filtration rate on non-(1-84) parathyroid hormone (PTH) detected by intact PTH assays*, Clin Chem. 2000; 46:697-703). It seems meanwhile accepted that some immunoreactive PTH fragments have a biological activity comparable with intact PTH peptides whereas others such as hPTH(3-34) seem to inhibit the effects of parathyroid hormone (see EP-A 0 349 545; Schmidt-Gayk et al. (1999) Osteologie forum, 5, 48-58), Suva et al. (1987) Science, 237, 893ff; EP 0 451 867). It has further been postulated that large inactive but immunoreactive non-(1-84) PTH fragments lead to erroneous determinations (LePage R. et al. (1998) Clin. Chem., 44, 805-809). Additionally, dipeptidyl peptidase-4 (DPP4) is expressed on the surface of many cell types and a rather indiscriminate serine exopeptidase. This led to the hypothesis of PTH being a substrate of DPP4 or a similar exoproteinase while the utmost two N-terminal amino acids are necessary for a cAMP-cyclase activity and binding of the PTH peptide to its receptor. Consequently, a also two-site immunoassays have been developed employing antibodies that can distinguish between aminoterminally "intact" PTH peptide chains and PTH peptides that are missing one or two amino acids at the utmost aminoterminus (see WO 2001/44818 (Armbruster et al), WO 96/10041 (Mägerlein et al); WO 2003/03986 (Hutchison J S)).

The discovery of oxidized PTH peptide chains in serum samples of uraemic patients has further led to the development of an immunoassay for determination of non-oxidized PTH (1-84) and biologically active fragments thereof (WO 2002/082092). Thus, there are plethora of immunoassays available for measuring parathyroid hormone in plasma and concentrations of various "bioactive" PTH peptide embodiments which are in some patient groups similar and other patient groups noticeably different. It would therefore be desirable to obtain reliable information on the patients' PTH status which allows an adaptation of the medication of kidney patients to reduce morbidity and mortality (see also Sprague S M et al, *The Case for Routine Parathyroid Hormone Monitoring*, Clin J Am Soc Nephrol, October 2012, as doi: 10.2215/CJN.04650512e; Goldsmith D J A, ebuttal: *The Case for Routine Parathyroid Hormone Monitoring* Clin J Am Soc Nephrol 8: 319-320, 2013. doi: 10.2215/CJN.10231012). The state of the art PTH measurement therefore represents a problem.

SUMMARY OF THE INVENTION

The problem is solved by a method of PTH monitoring and assessing which gives reliable information on how to adopt the drugs usually prescribed to CKD patients that interfere with PTH secretion. The use of these drugs are also guided by the international guidelines.

Consequently, the instant disclosure relates to a method of in vitro monitoring and assessing the need of a medication which interferes with the regulation of the parathyroid hormone level in a kidney patient subject to oxidative stress comprising the steps of purifying a sample of plasma or serum from said kidney patient from human PTH peptides oxidized at either methionine 8 or 18 or both or at tryptophan 22 by contacting said sample with an antibody which recognizes and specifically binds a three-dimensional epitope located between amino acids 3 to 34 of oxidized human PTH peptides but which antibody does not bind non-oxidized human PTH (1-84) and fragments thereof; determining the amount of immunoreactive human PTH (iPTH) peptides in said sample by an immunoassay based on antibodies against human PTH(1-84) and fragments thereof that contain at least the domains responsible for receptor binding and activation of the cAMP-cyclase located between amino acids 3 to 34 of the human PTH sequence; and obtaining a PTH status value (n-oxPTH value) for said kidney patient which includes the rate of immunoreactive human PTH (iPTH) peptides secreted by cells of the parathyroid gland into the circulation and the rate by which immunoreactive human PTH (iPTH) peptides are oxidized by the oxidative stress suffered by said patient; and comparing the PTH status value (n-oxPTH) with a reference value at which the morbidity and all-cause mortality is low to determine the need of a medication with respect to a regulation of the PTH status value or for supplementation of the patient with human parathyroid hormone or active fragments thereof or both. The method can be used in particular for a sample from a kidney patient subject to a hemodialysis treatment. Otherwise, the sample may be from a kidney patient afflicted of chronic kidney disease (CKD) or uremia or hyperparathyroidism.

The method preferably comprises the step of contacting said sample of plasma or serum with a solid phase having bound an antibody which recognizes and specifically binds a three-dimensional epitope located between amino acids 3 to 34 of oxidized human PTH peptides but which antibody does not bind non-oxidized human PTH (1-84) and fragments thereof.

The method comprises a determination of immunoreactive potent human PTH (iPTH) peptides which may encompass the use of a two-site immunoassay wherein one antibody is a monoclonal antibody that binds to a domain involved in the binding of the PTH peptide to PTH receptors 1 and 2. Alternatively, the determination may comprise the use of a two-site immunoassay wherein one antibody binds an antigenic determinant comprising the utmost aminoterminal amino acids valine and serine of the human PTH and the other antibody binds in the region between amino acids 14 to 34 of the human PTH sequence. In another embodiment, the determination of immunoreactive potent human PTH (iPTH) may comprise the use of a two-site immunoassay wherein one antibody binds an antigenic determinant comprising amino acids 1 to the 13 of the human PTH sequence.

The employed antibody against oxidized human PTH peptides selectively binds a three-dimensional epitope between amino acids 3 to 34 of the human PTH sequence which does not comprise the oxidized methionines at position 8 and/or 18. In other words, for analysis showed that the employed monoclonal antibody specific for oxidized human binds to a conformational epitope between amino acids 3 to 34 of the human PTH sequence which does comprise any one of the methionine sulfoxides or ethionine sulfones.

An aspect of the disclosure relates to a determination of the ratio of immunoreactive human PTH (iPTH) and the amount of PTH peptides bound by said antibody which recognizes and selectively binds a three-dimensional epitope located between amino acids 3 to 34 of oxidized human PTH peptides.

A further aspect relates to a kit comprising a solid phase with an antibody that recognizes and selectively binds a three-dimensional epitope located between amino acids 3 to 34 of oxidized human PTH peptides, and a combination of antibodies for determining the immunoreactive intact human PTH (iPTH) in plasma or serum as disclosed above.

The disclosed method usually comprises a purifying of a sample of plasma or serum from a patient from PTH peptides chains subject to oxidative stress and oxidized at either methionines 8 or 18 or both or at tryptophan 22 by contacting said sample with an antibody that binds an oxidized antigenic determinant of the human parathyroid hormone. PTH oxidation and hence inactivation is an issue in CKD patients with hemodialysis since these patients suffer from oxidative stress which interfere with conventional PTH measurements. The method further comprises a determination of the secreted parathyroid hormone status in said purified sample by an immunoassay that measures the concentration of those peptides of the human parathyroid hormone that contain at least the domains responsible for receptor binding and activation of the cAMP-cyclase so that a PTH status is obtained, hereinafter "n-oxPTH" status, that corresponds to the equilibrium of the rate of PTH peptides secreted by cells of the parathyroid gland into circulation and clearance of PTH peptides from circulation that have been oxidized by the oxidative stress through the hemodialysis treatment. The disclosed method then compares the measured n-oxPTH status with a n-oxPTH status at which the all-cause mortality hemodialysis patients is low to determine the need of a medication with respect to a regulation of the secreted parathyroid hormone or by a direct supplementation of parathyroid hormone.

The method comprises a contacting of said plasma sample with a solid phase having bound antibodies which bind an oxidized antigenic determinant of the human parathyroid hormone. The binding material may be in the form of a slurry.

According to a preferred aspect, the method comprises a use of a two-site immunoassay wherein one antibody is a monoclonal antibody that binds to a domain involved in the binding of the PTH peptide to PTH receptors 1 and 2. The antibody may be one which recognizes and selectively binds an epitope between amino acids 1 to 13 of the human parathyroid hormone as disclosed in WO 2003/003986 (Hutchison J S) or as described in WO 01/44818 (Armbruster F P et al) or in U.S. Pat. No. 6,030,790 (Adermann et al). Further suitable antibodies for determining the concentration of secreted potent human PTH peptides are disclosed in WO 00/42437.

In another embodiment the method comprises the use of a two-site immunoassay wherein one antibody binds an antigenic determinant comprising the utmost aminoterminal amino acids valine and serine of the human PTH and the other antibody binds in the region between amino acids 14 to 34 of the human PTH sequence.

In a preferred embodiment the antibody for purifying the immunoreactive potent PTH peptides recognizes a three-dimensional antigenic determinant located between amino acids 3 to 34 of the human parathyroid hormone which is formed by a change of peptide conformation following the oxidation of the native parathyroid hormone at either methionine in position 8 and/or 18 or at tryptophan in position 22. While no NMR data are available a skilled person will appreciate that the same change of PTH peptide conformation is brought about by a proteolytic removal of the utmost aminoterminal amino acids serine and valine so that such a conformation antibody will also remove such misfolded peptides. Whether the change of conformation leads synergistically to an oxidation of the peptide following oxidative stress remains to be elucidated. However, oxidation and change of conformation are indicative for the clearance rate of PTH from plasma.

An aspect of the invention relates to the testing of serum or plasma samples from a patient afflicted of chronic kidney disease. A further aspect relates to the testing of samples from uraemic patients or patients with hyperthyroidism.

BRIEF DESCRIPTION OF DRAWINGS

The present invention is best understood when read in conjunction with the accompanying tables and figures, which serve to illustrate the preferred embodiments. It is understood, however, that the invention is not limited to the specific embodiments disclosed in the figures.

DETAILED DESCRIPTION OF THE INVENTION

Figure 1:
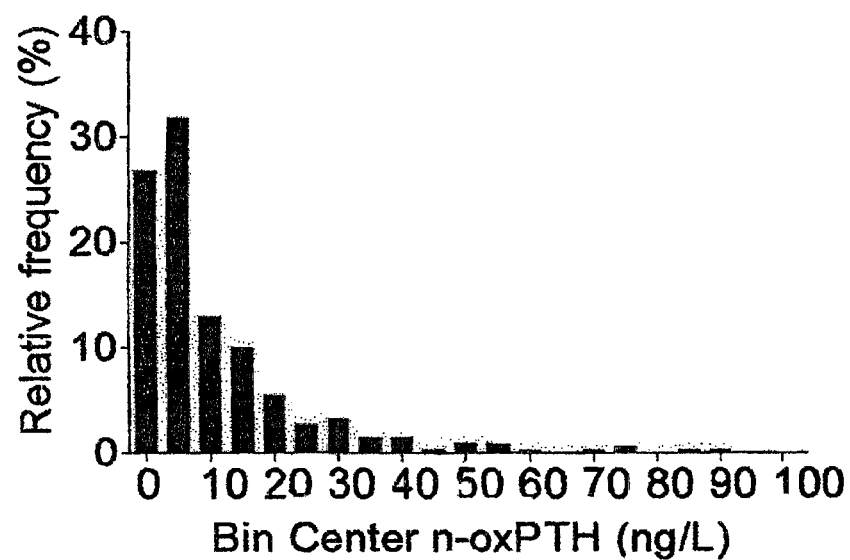
FIG. 1 is a diagram showing the relative frequency (%) distribution of measured serum values for a measured non-oxidized parathyroid hormone status (n-oxPTH) in 340 hemodialysis patients.

Animal studies have shown that oxidation of PTH at methionine residues results in a loss of biological activity. Any oxidative stress or a oxidative deactivation of the parathyroid hormone may be compensated or even over-compensated by an the increased secretion of parathyroid hormone into the circulation. Here, we disclose an oxidative stress parameter and its impact on the mortality in hemodialysis patients which gives rise to a therapeutic decision and specific medication. More precisely, the effects of non-oxidized intact immunoreactive PTH (n-oxPTH) and intact immunoreactive PTH (iPTH) in serum are compared and associated with the survival of hemodialysis patients.

"Intact PTH" is defined as the amount or concentration of immunoreactive PTH peptides when determined by a one or two-site immunoassay detecting the PTH peptide that contain at least the domains responsible for receptor binding and activation of the cAMP-cyclase. Those are located in the aminoterminal part of the PTH protein (hPTH(1-37)) The cAMP receptor-binding domain comprises the region from $His^{14}$ to $Phe^{34}$ and the DNA synthesis stimulating domain comprises $Asp^{30}$ to $Phe^{34}$. The complete aminoterminal peptide hPTH(1-34) is required for correct folding and stimulation of the cAMP-dependent signal pathway. The stimulatory potential is lost on deletion of $Ser^1$ and $Val^2$ but the cAMP-receptor binding capacity is not influenced by this deletion, indicating that the activation and receptor-binding sites are located in different domains.

The immunoreactive "intact PTH" as defined above is not synonymous with "bioactive PTH" since PTH bioactivity is affected by the correct folding of the PTH peptide chains and the absence of an oxidation of one or more methionines at positions 8 and/or 18 or at tryptophan 22. Despite numerous studies the routes for the bioactivity of the parathyroid hormone and its deactivation remain unclear and can hardly be correlated to a PTH peptide entity which is said to comprise the "effective bioactivity". The discordant disappearance of PTH bioactivity and plasma immunoreactivity in patients point to a dynamic PTH equilibrium so that a medication with PTH requires a determination of the momentary secretion rate of "intact PTH" activity and a momentary clearance rate of "oxPTH peptides" so that the disclosed n-oxPTH status measurement takes account of both PTH rates and can give directions for a suitable PTH medication required by the patient.

N-oxPTH measurements can be performed using test systems for the determination of "bioactive" PTH which have no clinically relevant cross-reactivity with the many C-terminal PTH degradation products, say hPTH(35-84) and fragments thereof. These are for example the Elecsys™ 2010 PTH immunoassay of Roche Diagnostics GmbH, Mannheim and the CAP-PTH-IRMA of the company Scantibodies. The electrochemiluminescence immunoassay employs a monoclonal captor antibody against an aminoterminal conformation epitope comprising amino acids 26 to 32 of hPTH and a ruthenium complex marked tracer antibody against a C-terminal hPTH epitope corresponding to the amino acids 55 to 64. The monoclonal captor antibody recognizes the inactive "large hPTH(7-84) fragment" but not bioactive hPTH-fragments such as hPTH(1-34), hPTH(1-35) or hPTH(1-37) (Gao P et al. 2000 Poster M455, ASBMR 22nd Annual Meeting, Roth H J et al. (2000), Poster P I 288; 11th International Congress of Endocrinology, Sydney). The CAP-PTH-IRMA of the company Scantibodies (Santee Calif., US) employs polyclonal antibodies against the N-terminal region of hPTH(1-6) which are described as not binding to the large PTH (7-84) fragments. Moreover, Quest Diagnostics Inc. Introduced a "Bio-Intact PTH test" and obtained FDA-clearance for it as it said to recognize the entire parathyroid hormone molecule, rather than fragments of the molecule, which has a tendency to break up. Currently, PTH measurement is often complicated by the presence of inactive PTH fragments in blood, which impacts the clinical utility of such testing. In recognizing the entire PTH molecule, which consists of an 84-amino acid chain, the Bio-Intact PTH assay has specificity for the N-terminal region of PTH, which is considered essential for the biological effect of PTH. The Bio-Intact PTH test uses proprietary antibodies which are described binding a three-dimensional epitope comprising amino acid 1-13. Whatever immunoassay is used for determining the secretion rate of hPTH into circulation the resulting hPTH status does not reflect the true PTH bioactivity because these immunoassay cannot take account of all relevant factors such as the routes of degradation, the multitude of active, partly active and inactive PTH fragments, nor of their differing half-lifes in serum or plasma.

The present application discloses that hemodialysis patients having n-oxPTH levels in the upper n-oxPTH tertile show an increased survival compared to patients of the lower n-oxPTH tertile. After multivariable adjustment higher n-oxPTH tertile reduced whereas higher age increased the odds for death in hemodialysis patients. The validity of the present disclosure is strengthened by the fact that stratification of iPTH data from our cohort into five categories according to international guidelines reveal that hemodialysis patients with target iPTH levels according to the guidelines have longer median survival compared to the other groups. The J-shaped survival pattern confirms results derived from iPTH-data from a large mortality meta-analysis. Current PTH-assays do not distinguish between secretion and clearance of PTH forms, although it is well-known that oxidation of PTH results in loss of its biological activity. Our analysis in a subgroup of hemodialysis patients showing iPTH above the upper normal range (70 ng/L) clearly separated the true effects of the hormone from the disastrous effects of increased clearance and oxidation. Increased clearance of immunoreactive PTH would be noted by most current immunoassays but not increased oxidation and deactivation. We observed that increased mortality in this subgroup depended on protein oxidation of iPTH as a surrogate of overall protein oxidation and oxidation associated impairment of protein function and structure but not on biologically active n-oxPTH.

Human PTH is secreted by the chief cells of the parathyroid glands as a polypeptide having 84 amino acids. After secretion into the circulation, the bioactive PTH peptides comprising the essential domains increase blood calcium by an activation of parathyroid hormone 1 receptor, present in high levels in bone and kidney, and the parathyroid hormone 2 receptor, present in high levels in the central nervous system, pancreas, testis, and placenta. The half-life of those bioactive PTH peptides is approximately 4 minutes only. It was known that also the oxidation of those PTH peptides may result in a loss of biological activity (Galceran T et al, in *Absence of biological effects of oxidized parathyroid hormone-(1-34) in dogs and rats*. Endocrinology. 1984; 115:2375-2378; Horiuchi N. *Effects of oxidation of human parathyroid hormone on its biological activity in continuously infused, thyroparathyroidectomized rats*. J Bone Miner Res. 1988; 3:353-358; Zull J E et al, in *Effect of methionine oxidation and deletion of amino-terminal residues on the conformation of parathyroid hormone*. Circular dichroism studies. J Biol Chem. 1990; 265:5671-5676). Indeed, many publications have been concerned with the effect of oxidation stress in the case of chronically kidney insufficient patients (Martin-Mateo M C et al (1999), Ren Fail 21:55-167; Hasselwander O et al (1998) Free Radic Res 29:1-11; Zoccali C et al. (2000) Nephrol Dial Transplant 15: Suppl. 2; Canaud B et al (1999) Blood Purif 17:99-106). Various working groups have investigated oxidized parathyroid hormone and its biological activity (Alexiewicz L M et al. (1990), J Am Soc Nephrol 1:236-244; Zull J E et al (1990) J Biol Chem 265:5671-5676; Pitts T O et al. (1988) Miner Electrolyte Metab 15: 267-275; Horiuchi N (1988) J Bone Miner Res 3:353-358; Frelinger A L et al. (1986) Arch Biochem Biophys 244: 641-649; Galceran T et al. (1984) Endocrinology 115, 2375-2378; Frelinger A L et al. (1984) J Biol Chem 259:5507-5513; O'Riordan J L H et al. (1974) J Endocr 63:117-124; Logue F C et al (1991) Ann Clin Biochem 28:160-166; Logue F C (1991b) J Immun Meth 39:159). The oxidation stress in dialysis patients and its consequence for morbidity and all-cause mortality have, however, not so far been investigated and recognized.

The so-called intact PTH (iPTH) and bio-intact sandwich assays do not differentiate between non-oxidized PTH peptide chains (n-oxPTH) and oxidized PTH peptide chains (oxPTH). Using mass spectroscopy we recently demonstrated that oxidative stress in hemodialysis patient may lead to an oxidation of human PTH in vivo and to a variety of inactive PTH products with oxidized methionine residues at positions 8 and/or 18 (Hocher B et al in *Measuring parathyroid hormone (PTH) in patients with oxidative stress—do we need a fourth generation parathyroid hormone assay?* PLoS One. 2012; 7:e40242). This discovery and the immunological distinction between non-oxidized and oxidized "intact" PTH peptide chains in plasma or serum which gives rise to a n-oxPTH status which allows a new medication of haemodialysis patients. Hereinafter, the term n-oxPTH is used for an immunoreactive "intact" PTH (iPTH) concentration as defined above in serum or plasma after taking account of the PTH clearance in serum or plasma by the oxidation of PTH peptide chains. Whether or not the measured n-oxPTH concentration represents the "true" PTH bioactivity present in serum is not relevant since we discovered that the all-cause mortality of hemodialysis patients is linked to the equilibrium of immunoreactive secreted intact PTH and PTH peptide chains which are immunoreactive for oxidation in the aminoterminal portion of PTH. Only after removal of those oxidized PTH chains, the resulting rate of secreted iPTH into the serum gives an in vitro parameter which allows a therapeutic decision as whether a therapy with vitamin D, phosphorus binders or calcimimetics needs adjustment to achieve treatment goals provided by international guidelines. The discovery of a dynamic PTH parameter which correlates with the all-cause mortality in hemodialysis patients then allows a reasonable medication and therapy. In the examples described below, the PTH concentration in serum as measured by means of a third generation intact-PTH immunoassay system (Elecsys™ 2010 PTH Roche), both directly (total intact parathyroid hormone, iPTH) and after removal of oxidized PTH molecules from the samples using a monoclonal antibody which binds oxidized human PTH peptide chains.

The hemodialysis patients (224 men/116 women) in our study had a median age of 66 years. 170 patients (50%) died during the follow up time of 5 years. Median n-oxPTH levels were higher in survivors (7.2 ng/L) compared to deceased patients (5.0 ng/L; p=0.002). Survival analysis showed an increased survival in the highest n-ox-PTH tertile compared to the lowest n-oxPTH tertile (Chi square 14.3; p=0.0008). Median survival was 1702 days in the highest n-oxPTH tertile, whereas it was only 453 days in the lowest n-oxPTH tertile. Multivariable-adjusted Cox regression showed that higher age increased odds for death, whereas higher n-oxPTH reduced the odds for death. Another model analyzing a subgroup of patients with secreted iPTH concentrations at baseline above the upper normal range of the iPTH assay (70 ng/L) revealed that mortality in this subgroup was associated with PTH oxidation but not with n-oxPTH levels. The huge numerical difference between the target PTH levels according to International Guidelines (PTH target=150 to 300 ng/L) and the median n-oxPTH value in survivors (7.2 ng/L) will not escape attention of the skilled reader and could not have been anticipated. In conclusion, the predictive powers of n-oxPTH and iPTH levels on mortality of hemodialysis patients differ substantially. Measurements of n-oxPTH therefore reflect the dynamic PTH hormone status more precisely. The iPTH associated mortality especially when iPTH levels are high reflects mainly mortality associated with PTH protein oxidation and oxidative stress. This gives rise to a new medication program and therapy. The skilled person will also appreciate that the degree of PTH oxidation and of a measurement of the inherent oxidative stress leads to new therapies and medication programs. Thus, the quantitative amount of oxidized PTH peptides within serum or plasma represents an important medical parameter which requires regulation and monitoring.

EXAMPLES

Example 1

PTH-Measurements

PTH was measured by means of a third-generation electrochemiluminescence PTH immunoassay system both directly (iPTH) and after prior removal of misfolded or oxidized PTH molecules from the samples using monoclonal antibodies raised against the oxidized human PTH (n-oxPTH). Removal of oxidized PTH was performed using an anti-human oxidized PTH monoclonal antibody as described below. The anti-human oxidized PTH monoclonal antibody was immobilized on CNBr-activated Sepharose 4B (GE Healthcare Bio-Sciences, Uppsala, Sweden). Hundred μl aliquot of the slurry as filled in a column (MobiSpinColumn, MoBiTec, Göttingen, Germany) and equilibrated with PBS buffer, pH 7.4. Then, 500 μl of plasma samples were applied on the columns which were incubated mixing end-over-end for 2 h at room temperature, washed with 250 μl of 0.1 M ammonium acetate buffer pH 7.0, followed by a wash with 250 μl of 0.1 M ammonium acetate buffer pH 7.0, containing 20% acetonitrile, and then eluted 2 times with 200 μl of elution buffer (0.05 M formic acid, pH 3.5). Flow-through was collected separately and lyophilized.

Then the samples were reconstituted in 500 μl of PBS buffer, pH 7.4 and aliquots analyzed for iPTH. The employed iPTH immunoassay (ECLIA Elecsys 2010; Roche Diagnostics, Mannheim, Germany) is based on a biotinylated monoclonal antibody, which reacts with amino acids 26-32, and a capture ruthenium-complexed monoclonal antibody, which reacts with amino acids 55-64. The determinations were performed on a Roche Modular E 170. The intra-assay CV was 4.1% and the inter-assay CV was 5.8% at concentrations of 35.0 and 180.0 ng/L, respectively.

Example 2

Monoclonal Antibodies Against a Conformation Epitope of Oxidized PTH(aa 1-38)

Monoclonal antibodies were raised in BALB/c-mice. The mice were immunized with the oxPTH(aa 1-38) thyreoglobulin conjugate at 200 μg for both primary and secondary immunizations with incomplete Freund's (mineral oil only) in the intraperitoneal cavity. Each of the antisera was tested for binding to non-oxidized biotin-hPTH(1-38). To detect antibodies specifically recognizing oxPTH(aa 1-38) peptides, we used the double antibody separation technique and as tracer biotin-oxPTH(aa1-38) labelled with $^{120}$I-streptavidin. After cell fusion and HAT selection, selected hybridomas were screened in the same way, namely for binding to human oxidized PTH(aa 1-84) but not to human PTH(1-84).

For ultimate characterization of the specificity of the monoclonal antibodies (MAB) and for identification of a monoclonal antibody recognizing a conformation epitope common to oxidized hPTH(1-38) peptides, say common to all forms of oxidized hPTH(aa 1-38) independently from oxidation status and chirality (Met-R—O, Met-S—O, and MetO$_2$ at positions 8, 18 and both), the antibody was immobilized on CNBr-activated Sepharose 4B (GE Healthcare Bio-Sciences, Uppsala, Sweden). Hundred μl aliquot of the slurry was filled in a column (MobiSpinColumn MoBiTec, Göttingen, Germany) and equilibrated with PBS buffer, pH 7.4. Then 2.5 μg of lyophilized oxidized hPTH (1-84) were dissolved in 300 μl of equilibrating buffer and applied on the column. The column was incubated end-over-end for 1 h at room temperature, washed with 300 μl of equilibrating buffer, followed by 3 washes with 300 μl of distilled water, and then eluted 2 times with 200 μl of elution buffer (0.1% TFA). Flow-through, wash fractions (equilibrating buffer and water) as well as eluate of the column were collected separately, lyophilized and analyzed by nanoLC-ESI-FT-MS. A monoclonal antibody ("oxPTH-ConforMAB") recognizing a conformation epitope present on all forms of oxidized hPTH(aa 1-84) and fragments thereof was selected for further analysis and characterization. The selected oxPTH-ConforMAB specifically recognized with high affinity all forms of oxidized and misfolded hPTH fragments, but not non-oxidized PTH (aa 1-84).

Example 3

Patients

A prospective cohort study in 340 hemodialysis patients was followed up for 5 years. Our eligibility criteria included all adult prevalent patients on hemodialysis treatment due to end-stage chronic kidney disease stage 5 and presence of informed consent. Informed consent from each patient and ethical approval by the local ethics committee were obtained. Data on dialysis vintage at inclusion and duration of hemodialysis treatment per session were obtained. All of the patients were routinely dialyzed for 4 to 5 hours three times weekly using biocompatible membranes with no dialyser re-use. Blood flow rates were 250 to 300 mL/min, dialysate flow rates were 500 mL/min, dialysate conductivity was 135 mS. Blood pressure was measured before dialysis. Predialysis blood samples were taken at study entry. Blood was collected immediately before the start of the hemodialysis session.

Clinical and laboratory data included age, gender, medications (use of angiotensin-converting-enzyme inhibitors, β-blockers, calcium channel blockers, and erythropoietin), body mass index (calculated as body weight divided by height squared), systolic and diastolic blood pressure, serum albumin, serum cholesterol, serum triglyceride, serum urea, serum creatinine, serum calcium, serum potassium, and serum phosphate.

was nephrosclerosis in 113 cases (33%), diabetic nephropathy in 107 cases (31%), chronic glomerular nephritis in 29 cases (9%), polycystic kidney disease in 9 cases (3%) and other/unknown in 82 cases (24%). The median n-oxPTH concentration was 5.9 ng/L (IQR, 2.4 to 14.0 ng/L). n-oxPTH concentrations were not different in men and women (5.9 ng/L; IQR, 2.4 to 14.2 ng/L; n=224; vs. 5.5 ng/L; IQR, 2.4 to 14.0 ng/L; n=116; p=0.915).

Table 1 summarizes the distribution of cases and laboratory variables stratified by tertiles of n-oxPTH. Tertile limits were n-oxPTH concentrations of 3.3 ng/L and 10.3 ng/L, respectively. Hemodialysis patients of the upper n-oxPTH tertile had higher weight, body mass index, and higher urea, a proxy for dietary protein intake, higher creatinine, a proxy for muscle mass, and typical signs of impaired mineral metabolism, i.e. lower serum calcium and higher serum phosphorous concentrations. Furthermore, serum phosphorus concentrations were directly (Spearman r=0.245; p<0.001) and serum calcium concentrations were inversely (Spearman r=−0.160; p=0.004) correlated with n-oxPTH concentrations. On the other hand, age (Spearman r=−0.099) and dialyses vintage (Spearman r=0.098) were not significantly correlated with n-oxPTH.

TABLE 1

Baseline clinical and biochemical characteristics of hemodialysis patients by tertiles of non-oxidized intact parathyroid hormone (n-oxPTH).

| CHARACTERISTIC | 1 TERTILE | 2. TERTILE | 3. TERTILE | P-VALUE |
| --- | --- | --- | --- | --- |
| Age (years) | 68 (57-76) | 67 (56-77) | 65 (54-72) | 0.125 |
| Gender (% Female) | 35% | 35% | 35% | 0.928 |
| Vintage (days) | 241 (31-1233) | 263 (58-913) | 425 (31-1507) | 0.429 |
| Diabetes mellitus (%) | 31% | 46% | 38% | 0.076 |
| Smoker (%) | 31% | 30% | 35% | 0.732 |
| Weight (kg) | 70 (60.0-80) | 70 (60-78) | 75 (67-85) | 0.003 |
| Body mass index (kg/m$^2$)$^b$ | 24.3 (21.1-26.5) | 24.1 (21.9-26.3) | 25.6 (22.9-29.4) | 0.003 |
| Systolic blood pressure (mmHg) | 134 (110-146) | 133 (112-149) | 138 (118-153) | 0.326 |
| Diastolic blood pressure(mmHg) | 69 (58-80) | 67 (57-80) | 72 (60-83) | 0.185 |
| Hemoglobin (mg/dL) | 10.0 (9.1-11.4) | 10.2 (9.3-11.2) | 10.5 (8.9-11.8) | 0.589 |
| Leukocytes (10$^9$/L) | 8.0 (5.9-10.1) | 8.4 (6.0-10.8) | 8.1 (6.3-11.3) | 0.895 |
| Platelets (10$^9$/L) | 218 (178-272) | 221 (167-275) | 230 (174-296) | 0.846 |
| Serum albumin (g/L) | 3.3 (2.9-3.7) | 3.3 (2.8-3.6) | 3.4 (2.9-3.8) | 0.371 |
| Serum cholesterol (mg/dL) | 152 (129-186) | 151 (125-190) | 150 (126-189) | 0.963 |
| Urea (mg/dL) | 69 (47-93) | 57 (48-89) | 77 (57-102) | 0.026 |
| Serum creatinine (mg/dL) | 5.5 (3.8-7.9) | 5.6 (3.7-7.9) | 7.1 (5.8-9.3) | 0.001 |
| Serum potassium (mmol/L) | 4.8 (4.0-5.3) | 4.5 (4.1-5.2) | 4.9 (4.2-5.3) | 0.238 |
| Serum calcium (mmol/L) | 2.30 (2.19-2.50) | 2.19 (2.06-2.37) | 2.22 (2.06-2.40) | 0.001 |
| Serum phosphorus (mg/dL) | 1.55 (1.07-1.91) | 1.43 (1.21-1.90) | 1.90 (1.36-2.30) | 0.001 |
| Dialysis dose (ktV) | 1.2 (1.1-1.3) | 1.2 (1.1-1.4) | 1.2 (1.0-1.4) | 0.227 |
| Angiotensin converting enzyme Inhibitors (%) | 26% | 26% | 26% | 0.992 |
| β-Blockers (%) | 60% | 60% | 60% | 0.996 |
| Calcium channel blockers (%) | 28% | 34% | 29% | 0.583 |
| Erythropoietin therapy (%) | 57% | 53% | 42% | 0.064 | a) Continuous variables are given as medians and interquartile range. Between groups, comparisons were made using non-parametric Kruskal-Wallis test for continuous variables and using Chi square test for categorical variables.
$^b$)Body mass index was calculated as weight in kilograms divided by height in meters squared.

170 patients (50%) died during the follow up time of 5 years. The causes of death were classified as cardiovascular including sudden death, infection, or cancer.

Example 4

Statistical Analysis of n-oxPTH Measurements

FIG. 1 shows the distribution of n-oxPTH concentrations in 340 hemodialysis patients (224 men and 116 women) with a median age of 66 years (IQR, 56 to 75 years), a median time since initiation of dialysis (dialysis vintage) of 266 days (IQR, 31 to 1209 days), and a median dialysis dose (kt/V) of 1.2 (IQR, 1.1 to 1.3). The cause of chronic kidney disease a) Continuous variables are given as medians and interquartile range. Between groups, comparisons were made using non-parametric Kruskal-Wallis test for continuous variables and using Chi square test or categorical variables.

b) Body mass index was calculated as weight in kilograms divided by height in meters squared.

Figure 2:
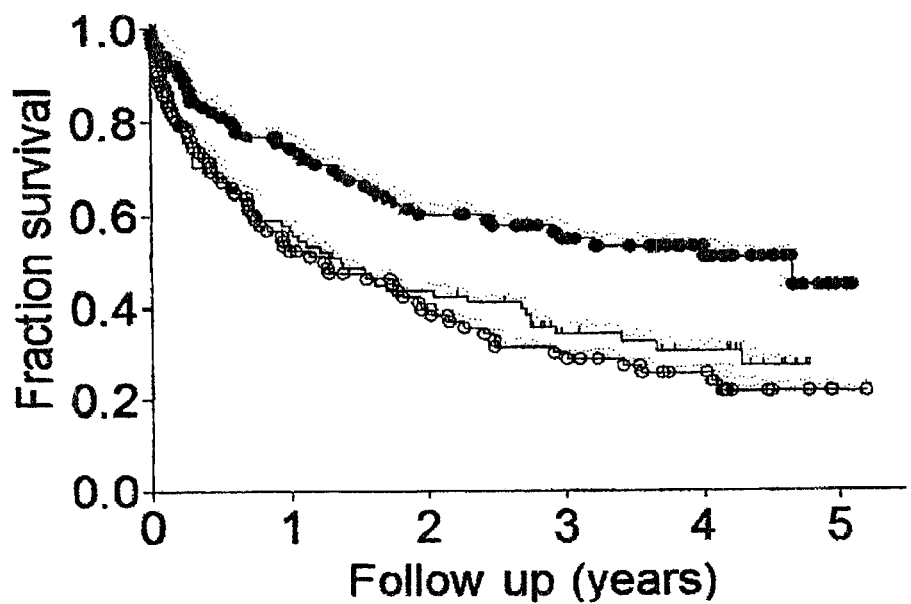
FIG. 2 is a diagram showing Kaplan-Meier survival curves for death in 340 hemodialysis patients; the patients were stratified into tertiles of measured non-oxidized parathyroid hormone (n-oxPTH) status concentrations (Log rank test, chi square=14.30; p=0.0008).

170 patients (50%) died during the follow up time of 5 years. Death occurred at a median of 217 days (IQR, 67 to 564 days) after study entry. The causes of death were cardiovascular diseases in 102 patients (60%), infections in 39 patients (23%), cancer in 19 patients (11%), and other/unknown reasons in 10 (6%). Median n-oxPTH levels were higher in survivors (7.2 ng/L; IQR 3.1 to 16.5 ng/L) compared to deceased patients (5.0 ng/L; IQR, 1.9 to 11.1 ng/L; p=0.002 by Mann Whitney test). Survival analysis showed an increased survival in the upper n-oxPTH tertile compared to the lower n-oxPTH tertile (Chi square 14.30; p=0.0008 by log-rank test). Median survival was 1702 days in the upper n-oxPTH tertile, whereas it was only 453 days in the lower n-oxPTH tertile (FIG. 2).

Multivariable-adjusted survival analyses were performed using the proportional hazards regression model with backward variable selection, using p<0.05 for variable retention. Variables tested were plasma n-oxPTH, iPTH category, dialysis dose, dialysis vintage, age, haemoglobin, and serum phosphorus. iPTH category, dialysis dose, dialysis vintage, and serum phosphorus did not show significant effects. This multivariable-adjusted Cox regression showed that that higher age increased odds or death, whereas higher n-oxPTH reduced the odds for death (Table 2).

TABLE 2

Multivariable-adjusted Cox regression showing the odds for death in hemodialysis patients.

| VARIABLE | B (SE) | ODDS RATIO | (95% CI) |
|---|---|---|---|
| n-oxPTH Tertile | −0.276 (0.103) | 0.759 | (0.620 to 0.929) |
| Age | 0.068 (0.008) | 1.070 | (1.053 to 1.087) |
| Hemoglobin | −0.169 (0.055) | 0.844 | (0.756 to 0.940) |

Multivariable-adjusted survival analyses were performed using the proportional hazards regression model with backward variable selection, using P < 0.05 for variable retention. Variables tested were plasma n-oxPTH, iPTH category, dialysis dose, dialysis vintage, age, hemoglobin, serum phosphorus.
iPTH category, dialysis dose, dialysis vintage, and serum phosphorus did not show a significant effects.

Figure 3:
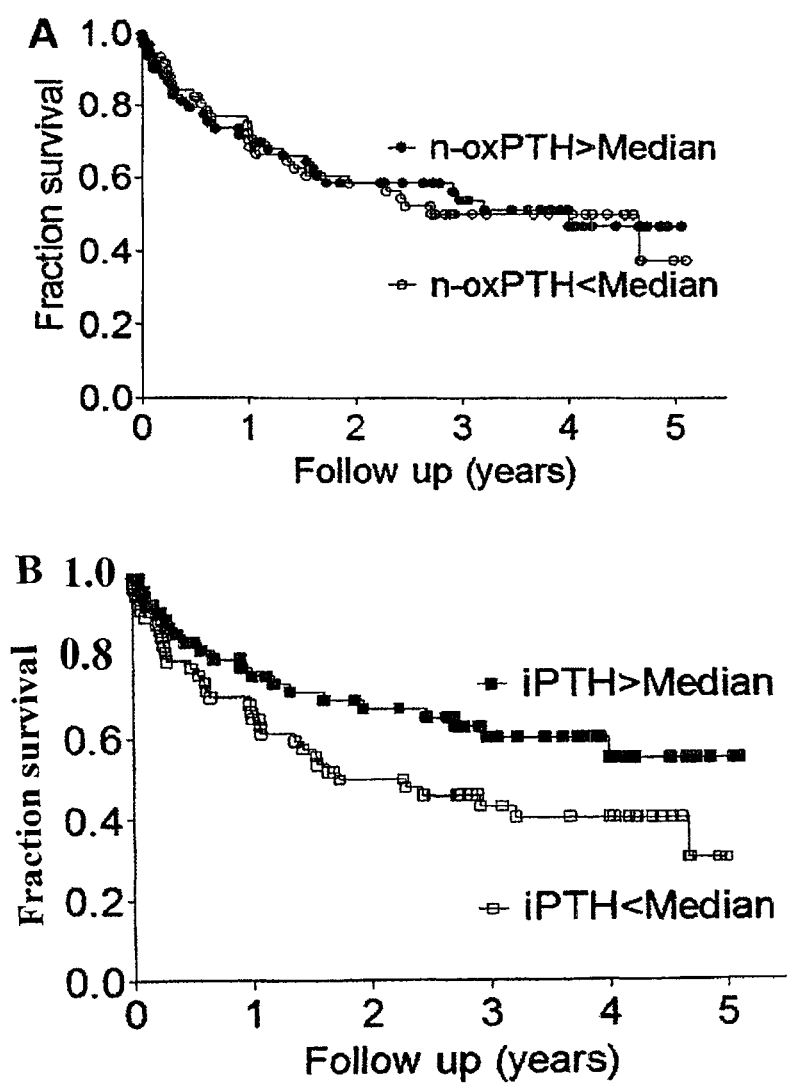
FIG. 3 are diagrams showing Kaplan-Meier survival curves for death in hemodialysis patients having a measured iPTH level higher than the normal iPTH range in healthy subjects (70 ng/L). (A) When the patients were stratified according to the median of measurable non-oxidized parathyroid hormone (n-oxPTH) status (Log rank test, chi square=0.046; p=0.80) the n-oxPTH status does not correlate with the patients' outcomes. (B) When the patients were stratified according to the median of iPTH concentrations (Log rank test, chi square=3.852; p=0.049) the oxidized PTH levels measured using the iPTH assay is predictive for the patients' outcome.

Furthermore, a model analyzing only patients with iPTH above the upper normal range (70 ng/L) revealed that mortality in this subgroup depended on protein oxidation of iPTH but not on biologically active n-oxPTH. In other words, n-oxPTH had no impact on mortality in patients with iPTH levels above the upper normal range, whereas in these patients iPTH was associated with all-cause mortality (FIG. 3).

Figure 4:
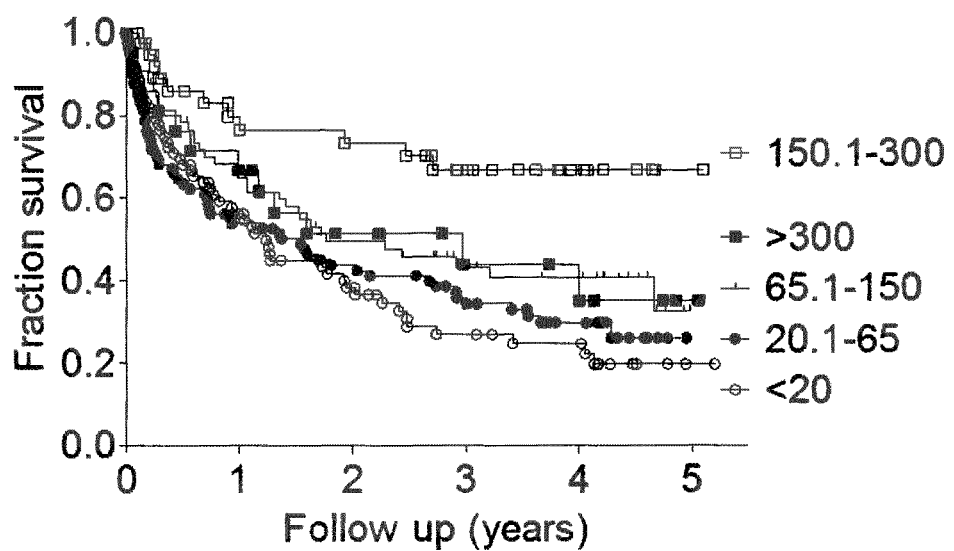
FIG. 4 is a diagram with Kaplan-Meier survival curves for death in 340 hemodialysis patients. According to international guidelines patients were stratified into five iPTH categories representing very low (<20 ng/L), low (20 to 65 ng/L), medium (65 to 150 ng/L), target (150 to 300 ng/L), and high (>300 ng/L) levels (Chi square 16.35; P=0.0026 by log-rank test). The J-shaped pattern between iPTH levels and outcome is characteristic for hemodialysis patients and thus indicates that the findings seen in the current study are of general applicability.

Using another model, we a priori stratified iPTH levels into five categories according to international guidelines, representing very low (<20 ng/L), low (20 to 65 ng/L), medium (65 to 150 ng/L), target (150 to 300 ng/L), and high (>300 ng/L). Survival analysis showed a J-shaped pattern, i.e. patients with target iPTH levels had longer median survival compared to the other categories (Chi square 16.35; P=0.0026 by log-rank test). This J-shaped pattern between iPTH levels and outcome is characteristic for hemodialysis patients, thereby confirming that our data were obtained from a typical hemodialysis cohort (FIG. 4).

Example 5

Statistical Analysis

Continuous variables were expressed as median with interquartile range (IQR) and compared with nonparametric Mann-Whitney test or non-parametric Kruskal-Wallis test and Dunn's multiple comparison post-hoc test, where appropriate. Associations between variables were tested using non parametric Spearman correlation. Time-to-event analyses were performed using the Kaplan-Meier method. Comparison of survival curves were performed using the log-rank (Mantel-Cox) test. Categorical variables were expressed as proportions and compared with the Chi-square test. Multivariable-adjusted survival analyses were performed using the proportional hazards regression model. Multivariable models were constructed with backward variable selection, using p<0.05 for variable retention. 45 patients (13%) underwent kidney transplantation during the follow up. These patients were censored on the day of transplantation. All hypothesis tests were 2-sided, with statistical significance defined as having a p value of less than 0.05. Statistical analyses were conducted using GraphPad Prism 5.0 (GraphPad Software San Diego, Calif.) or SPSS for windows (version 15; SPSS, Chicago, Ill.).

SUMMARY

The present application examines the dynamic equilibrium in plasma or serum between secreted intact PTH (iPTH), clearance of PTH activity by oxidation the and resulting parameter corresponding to non oxidized intact PTH (n-oxPTH) on the survival of hemodialysis patients. N-oxPTH measurements were performed with intact-PTH immunoassay after purifying the sample from oxidized PTH peptide chains. The present study indicates that hemodialysis patients in the upper n-oxPTH tertile enjoy increased survival compared to the patients in the lower n-oxPTH tertile. After multivariable adjustment higher n-oxPTH tertile reduced whereas higher age increased the odds for death in hemodialysis patients. The validity of the present disclosure is strengthened by the fact that stratification of iPTH data from our cohort into five categories according to international guidelines reveal that hemodialysis patients with target iPTH levels according to the guidelines had longer median survival compared to the other categories. This J-shaped survival pattern confirms results derived from iPTH-data from a large mortality meta-analysis. The analysis of a subgroup of hemodialysis patients showing iPTH above the upper normal range (70 ng/L) clearly separated the positive effects of secreted iPTH peptides from the negative effect of PTH peptides subjected to oxidation. The increased mortality in this subgroup depended on protein oxidation of iPTH.

A nephrologist familiar with this topic will appreciate that this analysis should be extended to dialysis patients with very high iPTH concentrations, which means patients who are considered to have secondary hyperparathyroidism according to classical diagnostic standards. The number of patients with such high iPTH concentrations in our study cohort was too low to allow clear statements. Analyses from cohorts of dialysis patients with secondary hyper-parathyroidism as investigated in the EVOLVE study cohort may help to address this important clinical question.

Current guidelines recommend to measure PTH levels routinely and to obtain target PTH levels (i.e. from 150 to 300 ng/L), because several studies observed worse outcome with PTH levels above 300 ng/L. In contrast we found that hemodialysis patients in the upper tertile, i.e. having n-oxPTH levels above 10.3 ng/L enjoying increased survival. This finding is surprising but while not wishing to be bound by any theory, there may be an explanation. The studied dialysis cohort comprised only a few patients with iPTH concentrations above 300 ng/L so that answers for this sub-cohort require a larger study group. Clearance of iPTH from plasma or serum occurs mainly by the liver and the kidney but there is evidence that the half-life of oxidized iPTH exceeds that of non-oxidized iPTH. In essence, the metabolic clearance rate of non-oxidized iPTH is the range of about 21.6 mL/min per kg body weight, whereas the metabolic clearance rate of oxidized iPTH is 8.8 mL/min per kg body weight only (Neuman W F et al in *The metabolism* of labeled parathyroid hormone. V. Collected biological studies. Calcif Tissue Res. 1975; 18:271-287; Hruska K A et al in *Peripheral metabolism of intact parathyroid hormone. Role of liver and kidney and the effect of chronic renal failure*, J Clin Invest. 1981; 67:885-892). Thus, high iPTH levels in the prior art literature may merely represent large amounts of oxidized PTH peptide chains and that patients were suffering from increased oxidative stress. Moreover, wasting may have an impact on the measurable immunoreactive intact PTH. Wasting is further associated with inflammation and oxidative stress. Thus the impact by wasting on the prior art intact PTH measurements is likely related to the presence of oxidized PTH peptides. However, this needs to be proven in future studies.

Removal of the parathyroid glands in animal models of uremia as well as in patients suffering from hyperparathyroidism proves that high concentrations of PTH contributes to vascular calcification, hence cardiovascular morbidity and mortality in uremia. At the same time, it is also true that oxidative stress is related to cardiovascular mortality in end-stage-renal disease patients as well. Our data indicate that the J-shaped survival curve for iPTH represents a overlay of two different biological processes. Conventional immunoreactive iPTH assays do either not differentiate between those PTH forms nor was the size of the oxidation stress on the PTH measurement appreciated. There was no knowledge how to use the information on the n-oxPTH status with respect to therapy and medication for CKD patients. In conclusion, the predictive power of immunoreactive n-oxPTH and iPTH for all cause mortality differ substantially. Thus, clinical decisions based on any immunoreactive PTH peptide concentration in plasma or serum may be misleading in patients with end-stage renal disease if the oxidative PTH clearance is not taken into account.

The invention claimed is:

1. A method of in vitro monitoring and assessing the need of a medication which interferes with the regulation of the parathyroid hormone (PTH) level in a kidney disease patient subject to oxidative stress, comprising the steps of:
   (i) obtaining a sample of plasma or serum from the kidney disease patient;
   (ii) purifying the sample of plasma or serum, the purifying comprising:
      (a) obtaining antibodies directed against oxidized human by immunizing a non-human animal with an immunogen comprising as hapten oxidized human PTH or a fragment thereof, and recovering said antibodies from said non-human animal;
      (b) screening and selecting first antibodies that bind to the amino acid sequence consisting of amino acids 1-38 of oxidized human PTH, wherein the first antibodies specifically (i) bind a three-dimensional epitope located between amino acids 3 to 34 of oxidized human PTH and (ii) do not bind non-oxidized human PTH (1-84) and fragments thereof; and
      (c) contacting the sample with a solid phase or slurry to which said selected first antibodies are bound to remove the human PTH oxidized peptides and obtain a purified sample;
   (iii) determining the amount of the oxidized human PTH peptides in the sample bound by the first antibodies;
   (iv) determining the amount of immunoreactive human PTH (iPTH) peptides in the sample by an immunoassay based on second antibodies against non-oxidized human PTH(1-84) and fragments thereof that contain at least the domains responsible for receptor binding and activation of the cAMP-cyclase located between amino acids 3 to 34 of the human PTH sequence;
   (v) obtaining a non-oxidized PTH (n-oxPTH) status value for the kidney patient which includes the rate of immunoreactive human PTH (iPTH) peptides secreted by cells of the parathyroid gland into the circulation and the subtraction of the rate by which immunoreactive human PTH (iPTH) peptides are oxidized by the oxidative stress suffered by the patient; and
   (vi) comparing the non-oxidized PTH status value (n-oxPTH) with a reference value at which the morbidity and all-cause mortality is low to determine the need of a medication with respect to a regulation of the PTH status value or for supplementation of the patient with human parathyroid hormone or active fragments thereof or both.

2. The method of claim 1, wherein the sample is from a kidney disease patient subject to a hemodialysis treatment.

3. The method of claim 1, wherein the sample is from a kidney disease patient afflicted of chronic kidney disease (CKD) or uremia or hyperparathyroidism.

4. The method of claim 1, wherein the determination of immunoreactive human PTH (iPTH) peptides comprises the use of a two-site immunoassay.

5. The method of claim 1, wherein the determination of immunoreactive human PTH (iPTH) peptides comprises the use of a two-site immunoassay wherein one antibody binds an antigenic determinant comprising the utmost aminoterminal amino acids valine and serine of the human PTH and the other antibody binds in the region between amino acids 14 to 34 of the human PTH sequence.

* * * * *